US006579524B1

(12) United States Patent
Corradin et al.

(10) Patent No.: US 6,579,524 B1
(45) Date of Patent: Jun. 17, 2003

(54) MALARIA VACCINE

(75) Inventors: Giampietro Corradin, Lausanne (SE); Mario Rogerro, Epalinges (CH)

(73) Assignee: RMF Dictagene S.A., Prilly (CH)

( * ) Notice: Subject to any disclaimer, the term of this patent is extended or adjusted under 35 U.S.C. 154(b) by 0 days.

(21) Appl. No.: 09/506,691

(22) Filed: Feb. 18, 2000

(30) Foreign Application Priority Data

Feb. 18, 1999 (EP) .......................................... 992004762

(51) Int. Cl.$^7$ ............................................. A61K 39/015
(52) U.S. Cl. ................. 424/191.1; 424/272.1; 530/300; 530/324
(58) Field of Search ........................... 424/184.1, 268.1, 424/272.1, 269.1, 265.1, 191.1; 530/300, 324, 820

(56) References Cited

FOREIGN PATENT DOCUMENTS

| EP | 329 257 | 8/1989 |
|----|---------|--------|
| WO | WO 90 00402 | 1/1990 |
| WO | WO 92 17204 | 10/1992 |
| WO | WO 94 06464 | 3/1994 |

OTHER PUBLICATIONS

Smooker et al. Vaccine 18 (2000) 2533–40, Abstract Only.*
Clyde, et al., "Immunization of Man Against Sporozite–Included Falciparum Malaria", *The American Journal of the Medical Sciences* 266(3):169–177 (1993).
Hoffman, et al., "Perspectives on Malaria Vaccine Development", in Malaria Vaccine Development, A Multi–Immune Response Approach, ASM Press, Washington, D.C. (1996).
Holder, A.A. "Malaria Vaccines", *Proc. Natl. Acad. Sci, USA* 96:1167–1169, Feb. 1999.

Nardin, et al., "T–Cell Responses to Pre–Erythrocytic Stages of Malaria: Role in Protection and Vaccine Development Against Pre–Eruthrocytic Stages," *Annu. Rev. Immunol.* (11):687–727 (1993).
Nussenzweig, et al., "Protective Immunity Produced by the Injection of X–irradiated Sporozoites of *Plasmodium berghei*", *Nature* 216:160–162, Oct. 14, 1967.
Richie, et al., "Progress and Challenges for Malaria Vaccines," *Nature* 415:694–701, Feb. 2002.
Syafruddin, et al., "Mutations in the Cytochrome b Gene of *Plasmodium berghei* Conferring Resistance to Atovaquone", *Molecular and Biochemical Parasitology* 104:185–194 (1999).
Vaidya, et al. "Structural Features of Plasmodium Cytochrome b That May Underlie Susceptibility ot 8–aminoquinolines and Hydroxynaphthoquinones", *Molecular and Biochemical Parasitology* 58:33–42 (1993).
Yap, et al. "Partial Nucleotide Sequence and Organisation of Extrachromosomal Plastid–Like DNA in *Plasmodium berghei*," *Gene* 200:91–98 (1997).
Dame JB et al: "Structure of the gene encoding the immunodominant surface antigen on the sporozoite of the human malaria parasite *Plasmodium falciparum*." Science, Aug. 10, 1984, 225 (4662) P593–9, XP000908559 United States (the whole document).

* cited by examiner

*Primary Examiner*—Patricia A. Duffy
(74) *Attorney, Agent, or Firm*—Marshall, Gerstein & Borun

(57) ABSTRACT

The present invention relates to a vaccine against malaria comprising a polypeptide having the amino acid sequence of the C-terminal part of the circumsporozoite protein of a Plasmodium species, in which polypeptide one or more pairs of cysteine residues are oxidized, and optionally a suitable carrier and/or adjuvant and/or biodegradable microcapsules for use in humans.

11 Claims, 5 Drawing Sheets

MALARIA VACCINE

Figure 1:
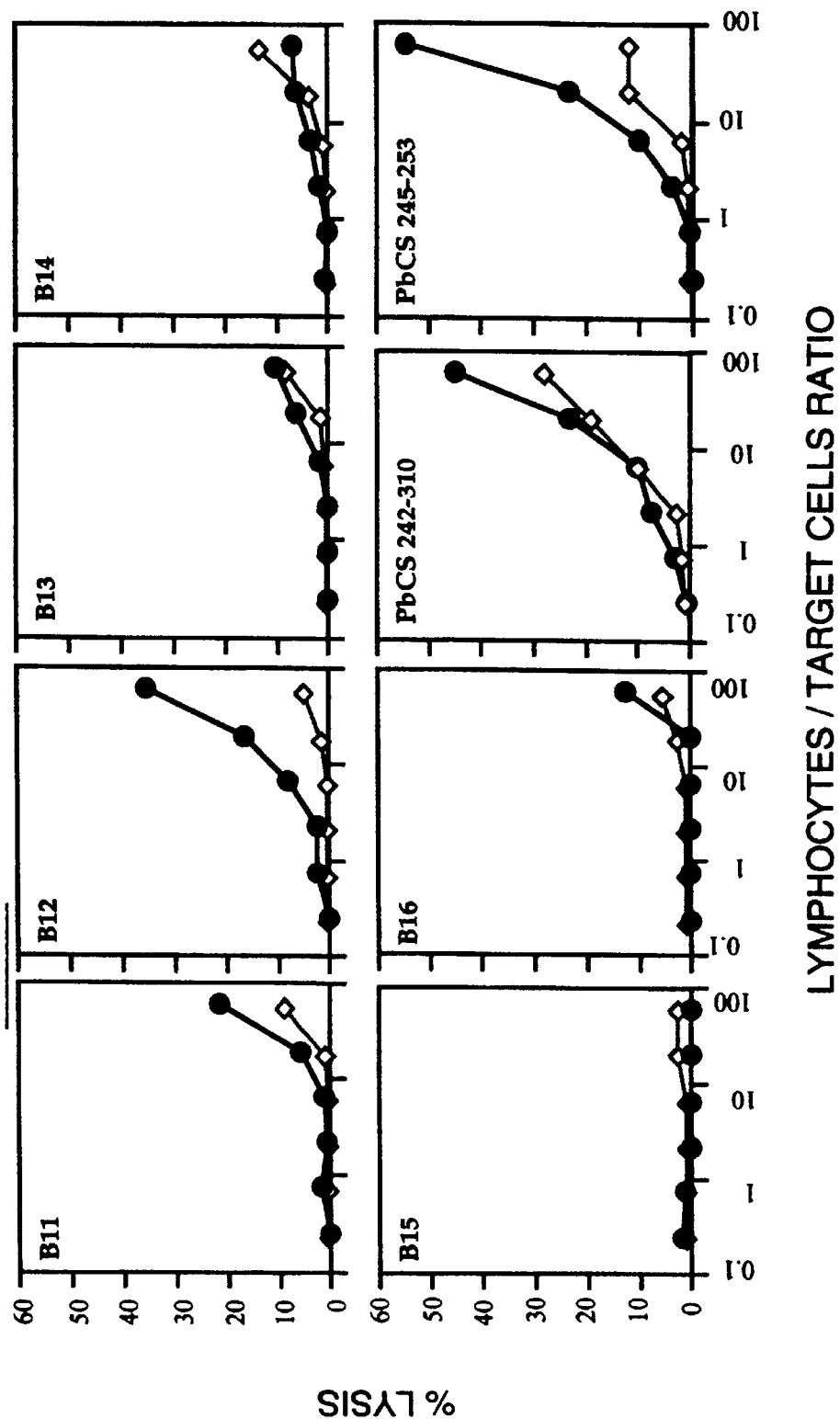

The present invention relates to a vaccine against malaria. The invention further relates to polypeptides that are capable of eliciting an immunological and protective response against malaria in a subject and the use thereof in prophylaxis.

Malaria is a parasitic disease transmitted during the blood meal of infected mosquitoes which inoculate sporozoites into the mammalian host. Within minutes, sporozoites invade hepatocytes and develop into merozoites intracellularly by asexual schizogony. The merozoites then invade red blood cells, producing the various symptoms associated with the disease. The life-cycle is completed when gametocytes are ingested during the blood meal of the mosquito vectors.

Protective immunity against malaria can be obtained by immunizing mice and humans with irradiation-attenuated sporozoites. This immunity is the result of the effect of neutralizing antibodies recognizing free sporozoites in the blood stream and of $CD4^+$ and $CD8^+$ T cells which prevent the development of the parasite hepatic forms. Experiments performed in B cell deficient mice have demonstrated that, despite the absence of anti-sporozoite antibodies, protection is induced by irradiated sporozoite immunization. This suggests that T cells specific for proteins present in the intracellular hepatic stage play a predominant role in protection. Therefore, one of the aims in malaria vaccine research is to mimic the protective immune response induced by injection of irradiated sporozoites.

In the research that led to the present invention it was found that a polypeptide of 69 amino acids (PbCS 242–310) encompassing the C-terminal region of the circumsporozoite protein of *Plasmodium berghei*, which was generated using solid-phase peptide synthesis elicited in BALB/c mice (M-2d) after two subcutaneous injections, in the presence of Incomplete Freund's Adjuvant (IFA) at the base of the tail, (i) high titers of anti-peptide antibodies which also recognize the native *P.berghei* CS protein, (ii) cytolytic T cells specific for the Major Histocompatibility Complex (MHC) antigen Kd restricted peptide PbCS 245–253, and (iii) partial $CD8^+$-dependent protection against sporozoite-induced malaria. The same frequencies of peptide PbCS 245–253 specific cytotoxic T lymphocytes (CTL) were found by IFN-γ ELISPOT in the draining lymph nodes of animals immunized with the short optimal CTL peptide 245–253 or with the polypeptide 242–310, indicating that the longer polypeptide can be processed and presented in vivo in the context of MHC class I as efficiently as short CTL peptides. Interestingly, even higher levels of CTL activity and protection were observed when the four cysteine residues present in the C-terminal peptide were fully oxidized. Theme findings underline the potential importance of the chemical nature of the C-terminal fragment on the activation of the immune system and concomitant protection. And more generally, as multiple facets of the immune system are stimulated by long synthetic polypeptides, these may provide a valuable alternative to vaccination with recombinant protein fragments or short peptides.

Based on this finding the present invention provides vaccines against malaria, in particular for use in humans, comprising a polypeptide having the amino acid sequence of the C-terminal part of the circumsporozoite protein of a Plasmodium species, which polypeptide at least comprises the four terminal cysteines from which at least one pair is oxidized, the vaccine optionally further comprising a suitable carrier and/or adjuvant and/or biodegradable microspheres. Biodegradable microcapsules are spheres of about 1 to 10 μm and very suitable carriers and/or adjuvants for the vaccine of the invention.

Specifically, the vaccine of the invention is based on the circumsporozoite protein of *Plasmodium falciparum*, more specifically of *Plasmodium falciparum* strain NF54.

Preferably the polypeptide in the vaccine consists of at least 42 consecutive amino acids derived from the C-terminal part of the circumsporozoite protein. More in particular, the invention relates to vaccines in which the polypeptide comprises at least the amino acids 342 to 383 of *Plasmodium falciparum*, even more in particular the amino acids 342 to 383 of the *Plasmodium falciparum* NF-54 strain.

Preferably, all four cysteines present in the polypeptide derived from the C-terminal part of the circumsporozoite protein of *Plasmodium falciparum* are oxidized.

It was found that the vaccine of the invention is in particular useful when the adjuvant is Montanide™. Montanide™ ISA Adjuvants (Seppic, Paris, France; ISA= Incomplete Seppic Adjuvant) are a group of oil/surfactant based adjuvants in which different surfactants are combined with either a non-metabolizable mineral oil, a metabolizable oil, or a mixture of the two. They are prepared for use as an emulsion with aqueous Antigen solution. The various Montanide ISA group of adjuvants are used as water-in-oil emulsions, oil-in-water emulsions, or water-in-oil-in-water emulsions. The different adjuvants accommodate different aqueous phase/oil phase ratios, because of the variety of surfactant and oil combinations. The performance of these adjuvants is said to be similar to Incomplete Freund's Adjuvant (IRA) for antibody production; however the inflammatory response is usually less.

The invention further relates to polypeptides having the amino acid sequence of the C-terminal part of the circumsporozoite protein of a Plasmodium species, which polypeptides comprise at least 42 consecutive C-terminal amino acids of which one or more cysteine pairs are oxidized.

In a particular embodiment of the invention the polypeptide comprises the amino acids 342 to 383 of *Plasmodium falciparum* NF-54 strain.

It is preferred that all cysteine residues present in the polypeptide are oxidized.

Furthermore, the invention relates to such polypeptide for use in a vaccine against malaria and to the use of such a polypeptide for the preparation of a vaccine against malaria.

The present invention will be further elucidated in the examples that follow, and which are in no way intended to be limiting to the invention.

Figure 2:
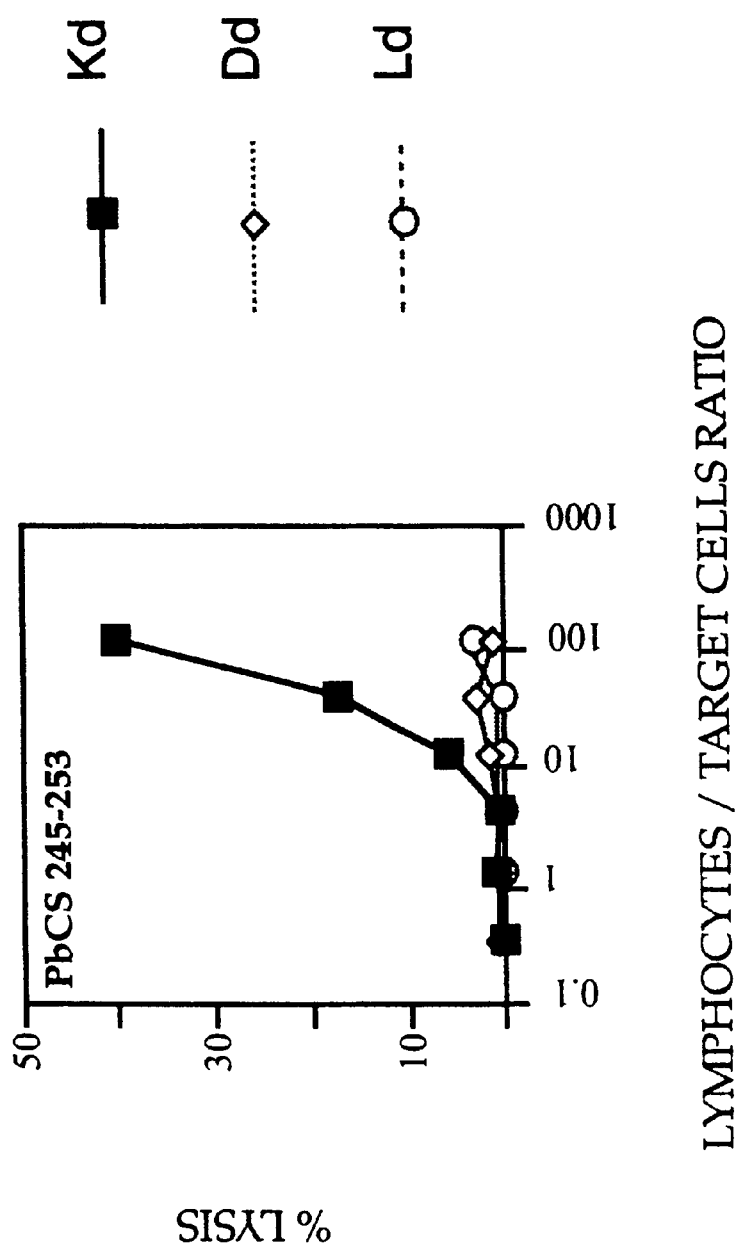

In the examples reference is made to the accompanying figures which show:

FIG. 1: Specificity of CTL bulk cultures obtained from spleen of mice immunized twice with 50 μg of peptide PbCS 242–310 in IFA. Specificity was determined 7 days after in vitro stimulation with the indicated peptide in a standard chromium release assay in the presence of target cells alone (open symbols) or pulsed with the corresponding peptide (filled symbols);

FIG. 2: Specificity of CTL bulk cultures of spleen cells isolated from mice immunized twice with peptide PbCS 242–310 in IFA; specificity was assessed 7 days after in vitro stimulation with the indicated peptide in a standard chromium release assay with L cells transfected with Kd, Dd or Ld and pulsed with the specific peptide.

Figure 3:
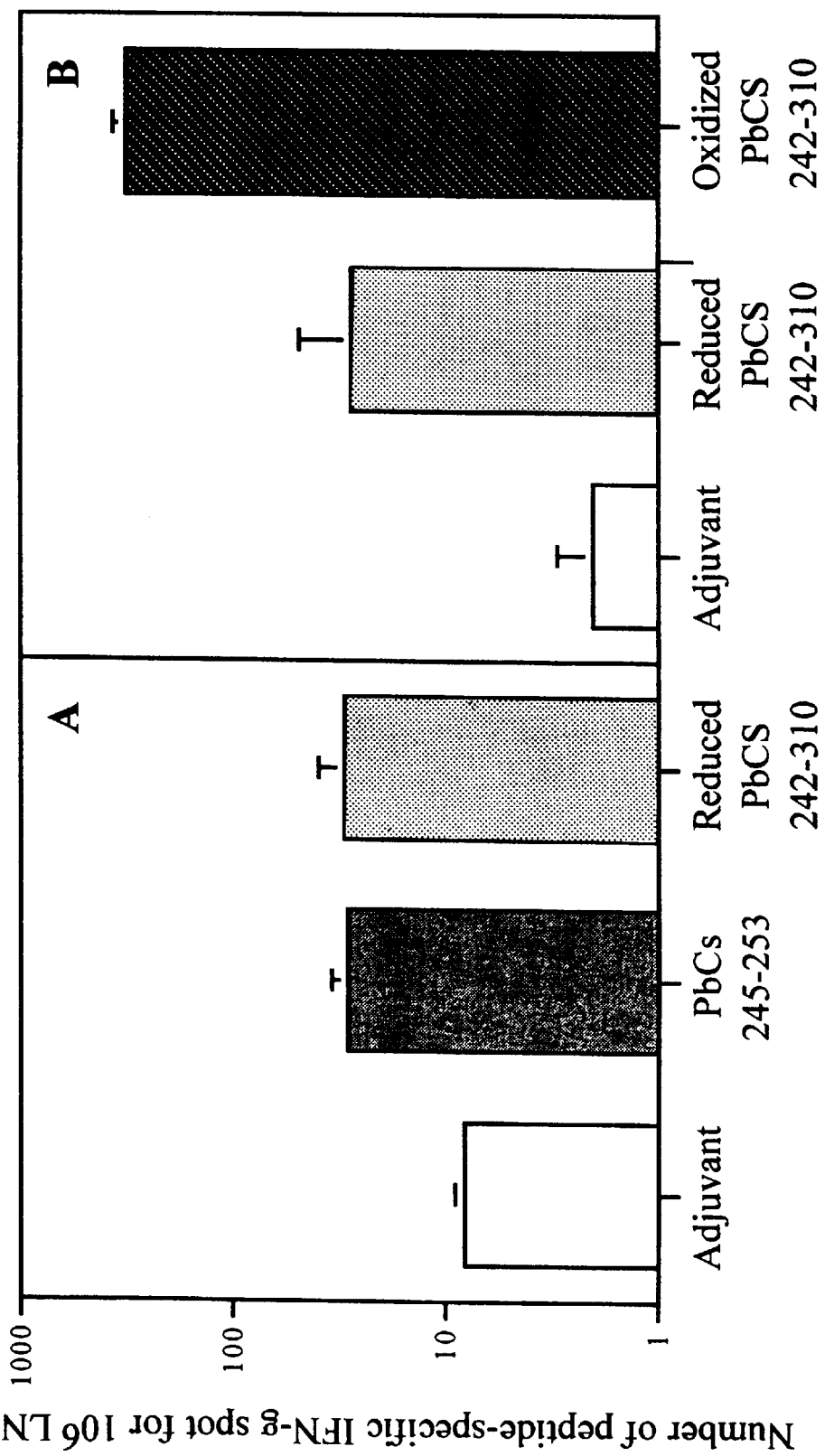
Figure 4:
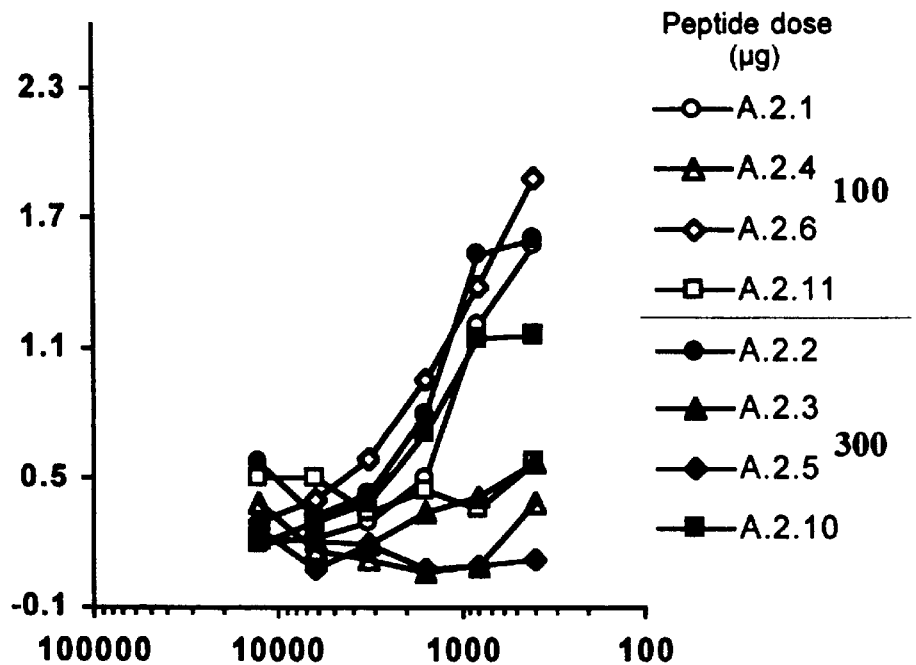
Figure 4:
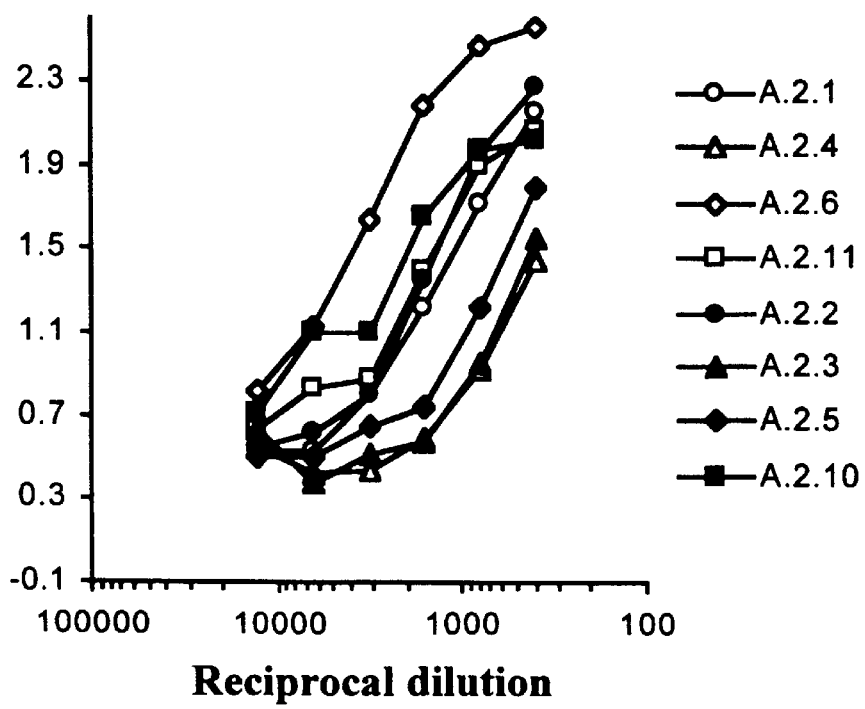

FIG. 3: The determination of peptide PbCS 245–253 specific T cells by IFN-γ ELISPOT, in lymph node (LN) cells. Mice were immunized with various antigen preparations in IFA at the base of the tail on day 0 and 3–4 weeks later. Panel A shows peptide PbCS 242–310 or peptides P30/PbCS 245–253, panel B shows reduced or oxidized PbCS 242–310. Inguinal and periaortic draining lymph nodes of two mice per group were removed 10–20 days after the second injection and cells obtained were pooled. The presence of specific T cells was assessed directly by ELISPOT in the presence of irradiated P815 cells pulsed or not with peptide PbCS 245–253. Mice immunized with IFA only were used as controls. Results are representative of three experiments performed and are expressed as the difference of spots obtained when cells were incubated with or without the PbCS peptide 245–252;

FIG. 4 Pf CS 282–383 specific antibodies evaluated one month after the first immunization. As in FIG. 2, the presence of Pf CS 282–383 specific antibodies was evaluated by ELISA in volunteers immunized in the presence of Montanide™ ISA-720 (upper panel) or Alum (lower panel), at two peptide doses (100 or 300 μg, filled or empty symbols, respectively).

Figure 5:
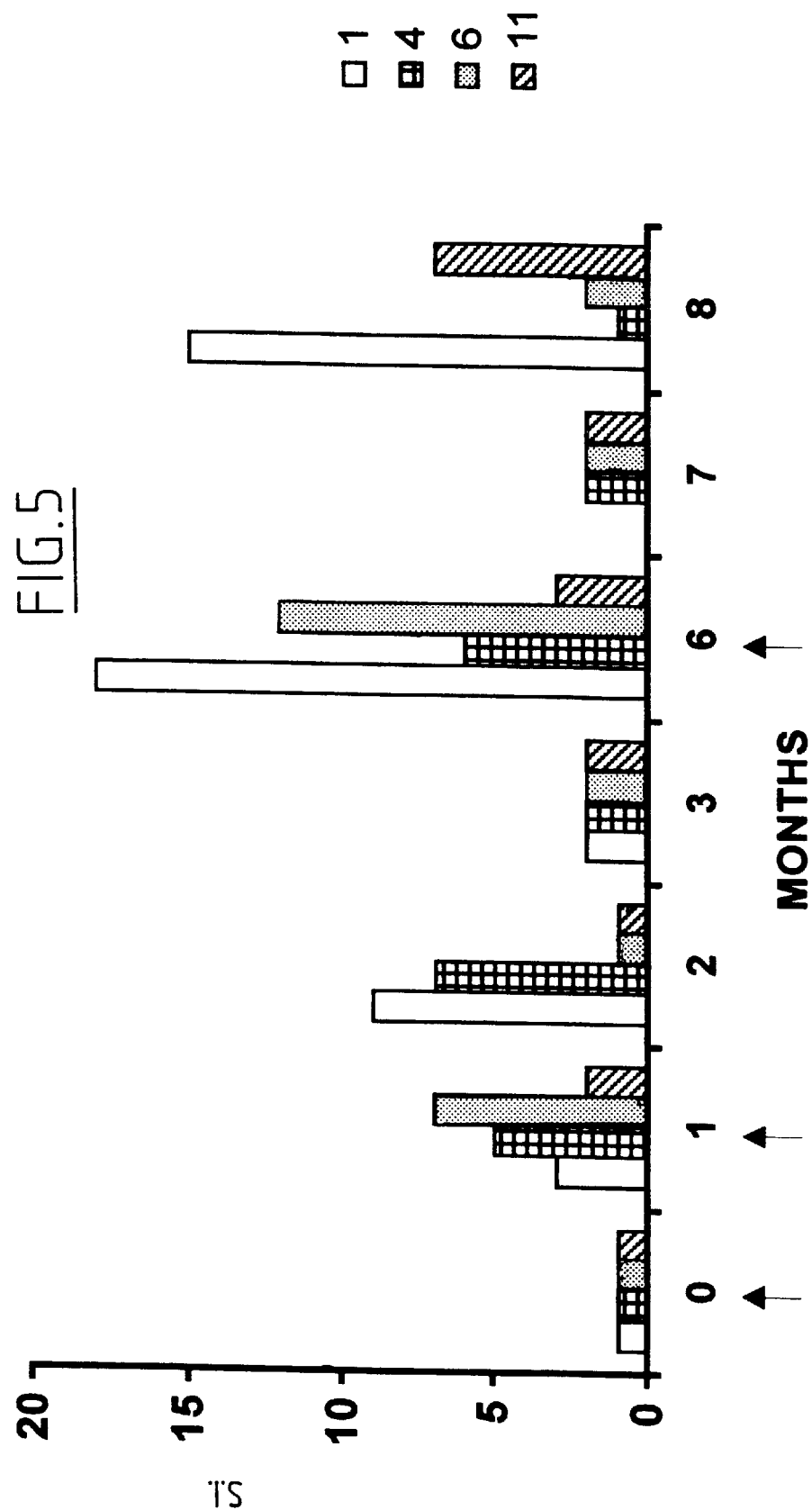

FIG. 5: Evolution of lymphocyte proliferation to Pf CS 282–383 in volunteers immunized with 100 μg of peptide in the presence of Montanide™ ISA-720. Peripheral Blood Lymphocytes (PBL) from 4 volunteers (Nos. 1, 4, 6 and 11) before (month 0) and after (months 1–8) immunizations were tested in a 6 day culture with Pf CS 282–383 at various concentrations (30–0.04 μg/ml). Data are shown as the highest average stimulation index (S.I.) of 5 replicate cultures. Control cultures (TT and PHA) gave satisfactory S.I. Arrows indicate time of injections, * not tested.

EXAMPLES

Example 1

Elevation of the Immune Response Against a Circumsporozoite Derived Polypeptide in a Murine Model Materials and Methods 1. Peptide Synthesis and Analysis All the peptides used in this example were chemically synthesized using solid phase F-moc chemistry, as described by Atherton et al. (Peptides Synthesis, Part 2. *Bioorg. Chem.* 8:350–351 (1979)). Chemicals and solvents used for the synthesis were purchased from Bachen Feinchemikallien (Buddendorf, Switzerland), Novabiochem (Läufelfingen, Switzerland) and Fluka (Buchs, Switzerland).

The 9-mer peptide PbCS 245–253 corresponds to an identified CTL epitope (Romero et al, *Nature* 341:323–326 (1989)). Polypeptide PbCS 242–310 covering the C-terminal region of the circumsporozoite protein of *Plasmodium berghei* ANKA strain (Lanar, *Mol. Bioch. Paras.* 39:151–153 (1990)) was obtained am previously described in detail for the *Plasmodium falciparum* analogue (Roggero et al., *Mol. Immunol.* 32:1301–1309 (1995)). Briefly, the polypeptide was prepared on a p-alkoxybenzylalcohol resin (Wang resin) with a degree of substitution of 0.4 mmol/g. A 10-fold excess of F-moc amino acid derivatives and a 30 min coupling time were used. The crude polypeptide was purified by a combination of size exclusion chromatography (Sephadex 025, Pharmacia, Sweden) and RP-HPLC (W-Porex 5 C4, 250×10 mm, Phenomenex, Rancho Palos Verdes, USA using a 10–50% CH$_3$CN gradient in 0.1% TFA/H$_2$O in 40 min with a flow rate of 3 ml/min).

The 20-mer peptides B11–B17 (Table 1) which overlap by 10 residues and encompass the sequence PbCS 233–312 were purified by size exclusion chromatography. The degree of purity of all peptides was analyzed by RP-HPLC (C18 analytical column). Amino acid composition of purified peptides was determined according to Knecht and Chang (*Anal. Chem.* 58:2375–2379 (1986)) and the molecular weight was confirmed by mass spectrometry on an LDI 1700 Mass Monitor (Linear Scientific Inc., Reno, Nev., USA) or a Voyager-DE (PerSeptive Byosystem, Framingham, Mass., USA).

2. Reduction and Oxidization of PbCS 242–310

The reduced form of PbCS 242–210 was obtained by treating the HPLC purified polypeptide with a 100 molar excess of DTT for 36 h at 37EC. After elimination of the DTT excess by size exclusion chromatography, a portion of the material was dissolved in 0.1 M CH$_3$COONH$_4$ pH 8.0 and left to air oxidize for 10 days. The complete reduction or oxidation of the peptide was confirmed both by the Ellman reaction and by adding a 1000 molar excess of N-ethylmaleimide (NEM) to an aliquot of the peptide solution. In the later case, after incubation at 4° C. for 1 h, no increase of the polypeptide MW was detected by mass spectrometry for the oxidized form while the reduced form presented a MW increase corresponding to the addition of four NEM molecules.

3. Immunization

Four- to five-weeks old female BALB/c mice were purchased from Harlan (Zeist, NL). Mice were injected subcutaneously at the base of the tail with 50 μg reduced or oxidized polypeptide dissolved in PBS and emulsified in incomplete Freund's adjuvant (IFA). For the short peptide PbCS 245–253, 4 μg were injected in combination with 100 μg of the universal helper peptide P30 (Renggli et al., *Immunol. Let.* 46:199–205 (1995)). Animals received a booster dose of immunogen after 2–3 weeks. Seven to ten days after the peptide boost, mice were bled to assess the production of specific antibodies. Subsequently, the animals were either sacrificed for proliferation, CTL or ELISPOT assays or exposed to sporozoite-bearing mosquitoes.

4. Parasite Challenge

*Plasmodium berghei* (ANKA strain; clone 1, Dr. Walliker, Edinburgh or clone Dr. P. H. Lambert, WHO, Geneva) sporozoites were produced by cyclical transmission to laboratory-bred *Anopheles gambiae* or *A. stephensi* mosquitoes. Mice were anaesthetized and exposed to infected mosquitoes. Mice were individually exposed to a previously determined number of bites necessary to obtain a complete infection in naive age-matched BALB/c mice. After parasite challenge, parasitemia was checked regularly from day 5 to day 14 by Giemsa-stained blood smears. Mice were considered protected when no parasites were detected 14 days after the challenge.

5. T Cell Depletion in vivo

Hybridomas H35 (CD8-specific rat IgG2b) (Golstein et al., *Immunol. Rev.* 68:5–42 (1982)) and GK1.5 (CD4-specific rat IgG2b) (Dialynas et al., *J. Immunol*, 131:2445–2451 (1983)) were used as a source for antibodies. Challenge was performed at day 0. One mg of CD4-specific antibodies was injected at days −3, −2 and −1 (same protocol for control Rat Ig's). Half mg of CD8-specific antibodies was injected at days −2 and +2.

Depletion was >95% during the time required for the complete development of *P. berghei* liver stages (Meis et al., *Am. J. Trop. Med. Hyg.* 37:506–10 (1987)). Depletion was verified by FACS (Becton Dickinson) analysis of peripheral blood lymphocytes (PBL) or spleen cells using CD4-specific FITC labelled (Ref. 1300 024, Boehringer Mannheim, Germany) and CD8-specific PE labelled (Ref. 1271 237, Boehringer Mannheim, Germany).

6. ELISPOT Assay

Nitrocellulose ELISPOT plates were coated overnight in a humid chamber at 4° C. with a PBS solution containing 100 µg/ml of IFN-γ-specific antibody OIE703B2 (Slade and Langhorne, *Immunobiology* 179, 353, (1989)). A saturation step was performed by adding DMEM containing 10% FCS for 2 hours at 37° C. Immune cells isolated from the draining lymph nodes of immunized mice were then co-cultured in the plates with 100,000 irradiated P815 cells/well pulsed or not with the short peptide PbCS 245–253, 24 hours at 37° C. Cells were then removed and a second IFN-γ specific biotinylated antibody (ANI) (Slade and Langhorne, *Immunobiology* 179, 353 (1989)) was added (1 µg/ml in PBS-1% BSA) for 2 hours at 37° C. After washing, streptavidin-alkaline phosphatase conjugate diluted in PBS-5% FCS was added for 1 hour at 37° C. and the presence of immune complexes revealed by the addition of BCIP/NBT substrate.

RESULTS

1. Immunological Response to the Fully Reduced PbCS 242–310 C-terminal Peptide

BALB/c mice were immunized twice with peptide PbCS 242–310 in IFA. The presence of peptide-specific antibodies was assessed 7–10 days after the second injection. A high titer of peptide-specific antibodies (1:300,000) was detected by ELISA and cross-reactivity with the native CS protein (1:25,000) was demonstrated by IFAT assays on *P.berghei* air-dried sporozoites. Recognition was specific since it was inhibited by the addition of competitor PbCS 242–310 peptide.

To assess the CTL response, spleen and LN immune cells were restimulated in vitro with the well known CTL epitope PbCS 245–253, peptide PbCS 242–310 and overlapping peptides B11–B17 covering the entire C-terminal sequence. High levels of cytotoxicity were detected in spleens and lymph nodes of immunized mice restimulated with peptides 245–253 and 243–262, whereas lower levels were induced by peptides 233–252 and 242–310 (FIG. 1, Table 1).

TABLE 1

Peptides used in the study

| Code | Sequence |
| --- | --- |
| B11 | 233–252 |
| B12 | 243–262 |
| B13 | 253–272 |
| B14 | 263–282 |
| B15 | 273–292 |
| B16 | 283–302 |
| B17 | 293–312 |
| PbCS 245–253 | 245–253 |
| PbCS 242–310 | 242–310 |

The cytotoxic activity was equivalent to that obtained in mice immunized with the optimal nonameric peptide PbCS 245–253 as determined by the numbers of IFN-γ spot forming cells (FIG. 1A). The Kd restriction of the CTL response was confirmed using transfected L cells expressing Kd, Dd or Ld MHC class I molecules (FIG. 2).

2. Immunization with PbCS 242–310 Peptide in IFA Confers CD8+-dependent Protection to BALB/c Mice Exposed to Parasite-bearing Mosquitoes BALB/c mice immunized twice subcutaneously at the base of the tail with 50 µg PbCS 242–310 peptide in IFA were submitted to a parasite challenge 7–10 days after the peptide boost. An important level of specific protection was obtained in PbCS 242–310 peptide-immunized mice (Table 2, Experiment A).

TABLE 2

| Experiment | Immunization | Treatment | Protected/Exposed | % Protection |
| --- | --- | --- | --- | --- |
| A | IFA | anal-CD4 | 2/9 | 22 |
|   | reduced PbCS 242-310 | anal-CD8 | 12/20 | 60 |
|   | reduced PbCS 242-310 |   | 3/20 | 15 |
|   | reduced PbCS 242-310 |   | 12/20 | 60 |
| B | IFA |   | 1/7 | 14 |
|   | oxidized PbCS 242-310 |   | 6/7 | 84 |
| C | IFA |   | 2/8 | 25 |
|   | reduced PbCS 242-310 |   | 4/8 | 50 |
|   | oxidized PbCS 242-310 |   | 8/8 | 100 |

In order to characterize the mechanisms of protection, T cell depletion was performed in vivo. Clearly, the depletion of CD4+ T cells did not significantly modify the observed protection. In contrast, depletion of CD8+ T cells by isotype matched CD8-specific antibodies prevented peptide-induced protection in vivo, since a baseline level of protection was observed (Table, Experiment A).

3. Immunological Properties of the Oxidized PbCS 242–310 C-terminal Peptide

The fully reduced C-terminal peptide was allowed to undergo full oxidation by air-exposing it in an aqueous solution at pH 8.0 for 10 days at room temperature. The immunological properties of this preparation were then compared with the fully reduced material in terms of CTL response and protective capacity. While there is no qualitative difference in antibody titers and T-cell proliferation, the number of IFN-γ ELISPOT obtained with the oxidized material in three different experiments was consistently greater than that observed for the fully reduced peptide (FIG. 3B). Similarly, the degree of protection obtained with the oxidized material was consistently higher than that observed with the reduced molecule (Table 2, Experiments B, C).

In this example injection of a long synthetic polypeptide covering the C-terminal region of the CS protein conferred CD8+-dependent protection against *Plasmodium berghei*. Interestingly, the CTL response against peptide PbCS 245–253 is elicited in both cases to a similar extent in immunized mice. In fact, the CTL frequencies determined by ELISPOT are similar in mice immunized either with the short PbCS 245–253 CTL peptide or the long PbCS 242–310 peptide. Since it is known that no protection is observed upon injection of the CTL epitope, the present experiments indicate that parasite specific T helper cells and antibodies specific for peptide PbCS 242–310 and the native CS protein also play a role in anti-parasite immunity.

It is known that T helper cells and antibodies can independently provide protection against malaria exoerythrocytic stages. This experiment shows that the peptide-specific antibodies also have the capability to recognize the native protein on *P.berghei* sporozoites and, therefore, it is assumed that they can neutralize sporozoites in vivo. This leads to a reduction in the number of infected hepatocytes and to protection, mediated by CD8+ T cells as a result of the modification of the balance between the hepatic stages and CD+ T cells in favor of these latter.

In addition to generating antibodies, injection of peptide PbCS 242–310 also induced Th1 cell proliferation (data not shown), although protection does not seem to be dependent on CD4+ T cells. Here, CD4+ T cells may play a crucial role in the initiation of a peptide-specific immune response by providing help to specific CTL or B cells.

The present results demonstrate that long polypeptides are efficient immunogens when injected in IFA. Here, immunization with peptide PbCS 242–310 not only generates a wide spectrum of immune responses but also provides CD8+-dependent protection against sporozoite-induced infection. In particular and unexpectedly, the oxidized material induces a higher number of CTL precursors and leads to a better degree of protection against a sporozoite challenge.

The data of this experiment were the foundation for using the oxidized CS terminal fragment of *P.falciparum* in an on-going Phase I human trial. The result obtained show that similar antibody, T cell proliferation and CTL responses are also obtained in humans (cf. Example 2).

Example 2

Immune Response in Humans Against the C-terminal Oxidized Fragment of the Circumsporozoite Protein of *Plasmodium falciparum*

1. Introduction

The synthetic peptide Pf CS 282–383 corresponding to the C-terminal end of the circumsporozoite protein of the *Plasmodium falciparum* NF-54 strain has being evaluated as a potential malaria vaccine; this study was initiated following pre-clinical studies that indicated its capacity to elicit antibodies, lymphocyte proliferation and cytotoxic T lymphocytes (CTL), as well as to protect from malaria infection in various animal models. The evaluation has been designed as an open, non-randomized, phase I clinical trial aimed at establishing the safety of the peptide, when injected in the presence of adjuvants.

2. Peptide Characteristics

The peptide was synthesized, purified and bottled sterilely in glass vials appropriate for every test dose. The quality of the preparation fulfills the criteria of a GLP product for human use.

3. Results

As seen in FIGS. 4 and 5 antibody response and T-cell proliferation are obtained after immunization of naive volunteers with 100 μg of antigen in Montanide™ ISA-720. Similarly, a CD8 dependent IFN-γ production is observed after immunization (Table 3).

Table 3 summarizes the results of an experiment in which the specific CD8 response was evaluated for HLA-A+ 0201 epitope of Pf CS NF54 (334–342) before immunization, 2 or 3 months after the secondhand 3 months after the third immunization. Specifically IFN-γ producing cells were enumerated by ELISPOT using different methods of spot counting in parallel, visual and 2 different ELISPOT readers (AID 1.2 and BioSys). Depending on the method of counting, different results were obtained.

TABLE 3

CD8 specific response in HLA-A* 0201 volunteers before and after the second and third immunizations

| Pf CS 334-342 | | before*** immunization | after the second immunization | after the third immunization |
|---|---|---|---|---|
| CD8 frequency* | mean response ± sd | 134 ± 165 | 845 ± 974 | 2046 ± 2433 |
| | range of positive responses | — | [1017; 1542] | [967; 7567] |
| Responders** | good responders | 0/8 | 2/8 | 5/8 |
| | intermediate responders | 4/8 | 5/8 | 2/8 |
| | non-responders | 4/8 | 1/8 | 1/8 |

*number of specific CD8 cells/million CD8; mean value for 8 HLA-A* 0201 volunteers and range of responses in good responders
**the 8 volunteers were determined as good or non-responders when the methods of counting gave all positive or negative responses, respectively, and as intermediate responses when non-concording
***analysis with frozen cells; at other time points, analyses were performed with fresh cells In conclusion, the present examples provide evidence that long synthetic polypeptides represent a valuable alternative for the production of vaccines capable of stimulating multiple facets of the immune system.

What is claimed is:

1. A composition which elicits a neutralizing antibody response and/or a CD8+ specific response against malarial parasites upon in vivo administration to a human subject comprising a polypeptide and a carrier, wherein said polypeptide has an amino acid sequence which:
   (a) is at least 42 residues in length and no more than 69 residues in length;
   (b) correspond to a sequence in the C-terminal 69 amino acids of the circumsporozoite protein of a Plasmodium species; and
   (c) has at least 4 cysteine residues, at least one of which is oxidized.

2. The composition of claim 1, wherein said circumsporozoite protein is of *Plasmodium falciparum*.

3. The composition of claim 2, wherein said circumsporozoite protein is of *Plasmodium falciparum* strain NF54.

4. The composition of claim 3, wherein said polypeptide is 42 residues in length and has a sequence corresponding to amino acids 342 to 383 of *Plasmodium falciparum* strain NF54.

5. The composition of any one of claims 1–4, wherein all of the cysteines in said polypeptide are oxidized.

6. The composition of any one of claims 1–4, wherein the carrier is the adjuvant MONTANIDE™ (mannide monooleate in mineral oil).

7. A polypeptide for use in eliciting a neutralizing antibody response and/or CD8+ specific response against malarial parasites upon in vivo administration to a human subject, wherein said polypeptide has an amino acid sequence which:
   (a) is at least 42 residues in length and no more than 69 residues in length;
   (b) corresponds to a sequence in the C-terminal 69 amino acids of the circumsporozoite protein of a Plasmodium species; and
   (c) has at least 4 cysteine residues, at least one of which is oxidized.

8. The polypeptide of claim 7, wherein said circumsporozoite protein is of *Plasmodium falciparum*.

9. The polypeptide of claim 8, wherein said circumsporozoite protein is of *Plasmodium falciparum* strain NF54.

10. The polypeptide of claim 9, wherein said polypeptide is 42 residues in length and has a sequence corresponding to amino acids 342 to 383 of *Plasmodium falciparum* strain NF54.

11. The polypeptide of any one of claims 7–10, wherein all of the cysteines in said polypeptide are oxidized.

* * * * *